(12) United States Patent
Miller

(10) Patent No.: US 7,458,940 B2
(45) Date of Patent: Dec. 2, 2008

(54) BIOPSY APPARATUS

(75) Inventor: Michael E. Miller, Trafalgar, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 204 days.

(21) Appl. No.: 10/903,305

(22) Filed: Jul. 28, 2004

(65) Prior Publication Data

US 2005/0027210 A1  Feb. 3, 2005

Related U.S. Application Data

(60) Continuation-in-part of application No. 10/848,278, filed on May 18, 2004, which is a division of application No. 09/707,022, filed on Nov. 6, 2000, now Pat. No. 6,758,824.

(60) Provisional application No. 60/490,916, filed on Jul. 29, 2003.

(51) Int. Cl.
  A61B 1/00 (2006.01)
  A61B 17/20 (2006.01)
  A61B 17/32 (2006.01)
  A61B 17/34 (2006.01)
  A61N 1/30 (2006.01)
  A61M 1/00 (2006.01)
  A61M 5/178 (2006.01)

(52) U.S. Cl. ............ 600/568; 600/567; 600/564; 600/566; 604/19; 604/22; 604/27; 604/35; 604/164.01; 604/164.02; 604/164.11; 604/166.01; 606/167; 606/170; 606/171; 606/179; 606/180

(58) Field of Classification Search ............ 600/567, 600/564, 566; 604/19, 22, 27, 35, 164.01, 604/164.02, 164.11, 166.01; 606/167, 170, 606/171, 179, 180
See application file for complete search history.

(56) References Cited

U.S. PATENT DOCUMENTS

| | | | |
|---|---|---|---|
| 3,401,684 A | 9/1968 | Dremann | |
| 3,456,806 A | 7/1969 | Borston | |
| 3,561,429 A | 2/1971 | Jewett et al. | |
| 3,815,604 A * | 6/1974 | O'Malley et al. | 604/22 |
| 3,889,657 A * | 6/1975 | Baumgarten | 600/571 |
| 3,937,222 A | 2/1976 | Banko | |
| 3,938,505 A | 2/1976 | Jamshidi | |
| 3,945,375 A | 3/1976 | Banko | |
| 3,994,297 A | 11/1976 | Kopf | |

(Continued)

OTHER PUBLICATIONS

PCT International Search Report, PCT/US2004/024873 dated Jul. 29, 2004.

(Continued)

*Primary Examiner*—Max Hindenburg
*Assistant Examiner*—Jeffrey G Hoekstra
(74) *Attorney, Agent, or Firm*—Rader, Fishman & Grauer PLLC

(57) ABSTRACT

A biopsy apparatus having a disposable cutting element and a reusable handpiece is disclosed. The disposable cutting element includes an inner cannula that defines an inner lumen and terminates in a cutting edge. The inner cannula is slidably disposed within an outer cannula that defines an outer lumen that has a tissue-receiving opening. The inner cannula is driven by a rotary motor and a reciprocating motor. Both motors are constructed of a MRI compatible material.

26 Claims, 2 Drawing Sheets

U.S. PATENT DOCUMENTS

| | | | |
|---|---|---|---|
| 4,007,742 A * | 2/1977 | Banko | 604/31 |
| D243,559 S | 3/1977 | Hoyle et al. | |
| 4,019,514 A | 4/1977 | Banko | |
| 4,101,756 A | 7/1978 | Yamano | |
| 4,117,843 A | 10/1978 | Banko | |
| 4,159,773 A | 7/1979 | Losenno | |
| 4,167,943 A | 9/1979 | Banko | |
| 4,167,944 A | 9/1979 | Banko | |
| 4,210,146 A | 7/1980 | Banko | |
| 4,257,425 A | 3/1981 | Ryan | |
| 4,308,878 A | 1/1982 | Silva | |
| 4,316,465 A * | 2/1982 | Dotson, Jr. | 604/22 |
| 4,354,093 A | 10/1982 | Zago | |
| 4,368,734 A | 1/1983 | Banko | |
| 4,513,745 A | 4/1985 | Amoils | |
| 4,530,356 A * | 7/1985 | Helfgott et al. | 606/171 |
| 4,533,818 A | 8/1985 | Green | |
| 4,549,554 A | 10/1985 | Markham | |
| 4,562,838 A | 1/1986 | Walker | |
| 4,644,951 A | 2/1987 | Bays | |
| 4,651,753 A | 3/1987 | Lifton | |
| 4,696,298 A | 9/1987 | Higgins et al. | |
| 4,708,147 A | 11/1987 | Haaga | |
| 4,803,341 A | 2/1989 | Barowski et al. | |
| 4,817,631 A | 4/1989 | Schnepp-Pesch et al. | |
| 4,850,373 A | 7/1989 | Zatloukal et al. | |
| 4,871,074 A | 10/1989 | Bryson et al. | |
| 4,919,146 A | 4/1990 | Rhinehart et al. | |
| 4,926,877 A | 5/1990 | Bookwalter | |
| RE33,258 E | 7/1990 | Onik et al. | |
| 4,973,019 A | 11/1990 | Baird et al. | |
| 4,985,027 A | 1/1991 | Dressel | |
| 5,027,827 A | 7/1991 | Cody et al. | |
| 5,031,778 A | 7/1991 | Edgecombe | |
| 5,054,615 A | 10/1991 | Stillwagon et al. | |
| 5,074,311 A * | 12/1991 | Hasson | 600/567 |
| 5,090,649 A | 2/1992 | Tipp | |
| 5,124,532 A | 6/1992 | Hafey et al. | |
| 5,141,189 A | 8/1992 | Andrew | |
| D329,304 S | 9/1992 | Tipp | |
| 5,172,701 A | 12/1992 | Leigh | |
| D332,670 S | 1/1993 | McFarland | |
| 5,183,052 A | 2/1993 | Terwilliger | |
| 5,213,110 A | 5/1993 | Kedem et al. | |
| D342,585 S | 12/1993 | Fischbach et al. | |
| 5,275,609 A * | 1/1994 | Pingleton et al. | 606/170 |
| 5,285,795 A | 2/1994 | Ryan et al. | |
| 5,295,890 A | 3/1994 | Ersek | |
| 5,295,980 A | 3/1994 | Ersek | |
| 5,348,022 A | 9/1994 | Leight et al. | |
| 5,403,276 A | 4/1995 | Schechter et al. | |
| 5,411,513 A | 5/1995 | Ireland et al. | |
| 5,423,844 A | 6/1995 | Miller | |
| 5,429,138 A | 7/1995 | Jamshidi | |
| 5,456,267 A | 10/1995 | Stark | |
| 5,458,112 A | 10/1995 | Weaver | |
| 5,464,300 A | 11/1995 | Crainich | |
| 5,520,635 A | 5/1996 | Gelbfish | |
| D371,220 S | 6/1996 | Behrens | |
| 5,526,822 A * | 6/1996 | Burbank et al. | 600/567 |
| 5,575,293 A | 11/1996 | Miller et al. | |
| 5,580,347 A | 12/1996 | Reimels | |
| D377,996 S | 2/1997 | Gilbert | |
| 5,615,782 A | 4/1997 | Choe | |
| D379,554 S | 5/1997 | Landers | |
| 5,643,304 A | 7/1997 | Schechter et al. | |
| 5,649,547 A * | 7/1997 | Ritchart et al. | 600/566 |
| 5,669,876 A | 9/1997 | Schechter et al. | |
| 5,669,923 A * | 9/1997 | Gordon | 606/170 |
| D386,818 S | 11/1997 | Boomfield | |
| 5,685,840 A | 11/1997 | Schechter et al. | |
| 5,730,717 A | 3/1998 | Gelbfish | |
| 5,769,086 A | 6/1998 | Ritchart et al. | |
| 5,775,333 A * | 7/1998 | Burbank et al. | 600/567 |
| 5,782,849 A | 7/1998 | Miller | |
| 5,788,651 A | 8/1998 | Weilandt | |
| 5,794,626 A * | 8/1998 | Kieturakis | 600/567 |
| 5,794,799 A | 8/1998 | Collins et al. | |
| 5,800,362 A | 9/1998 | Kobren et al. | |
| 5,810,806 A | 9/1998 | Ritchart et al. | |
| 5,817,033 A * | 10/1998 | DeSantis et al. | 600/562 |
| 5,843,111 A * | 12/1998 | Vijfvinkel | 606/171 |
| 5,848,978 A * | 12/1998 | Cecchi | 600/567 |
| D403,810 S | 1/1999 | Owens | |
| 5,893,862 A * | 4/1999 | Pratt et al. | 606/170 |
| 5,911,701 A | 6/1999 | Miller et al. | |
| 5,913,857 A | 6/1999 | Ritchart et al. | |
| 5,916,229 A | 6/1999 | Evans | |
| 5,928,164 A * | 7/1999 | Burbank et al. | 600/567 |
| 5,928,218 A | 7/1999 | Gelbfish | |
| 5,944,673 A | 8/1999 | Gregoire et al. | |
| 5,964,716 A * | 10/1999 | Gregoire et al. | 600/564 |
| 5,971,939 A * | 10/1999 | DeSantis et al. | 600/562 |
| 5,980,469 A * | 11/1999 | Burbank et al. | 600/567 |
| 5,980,546 A | 11/1999 | Hood | |
| 5,997,560 A | 12/1999 | Miller | |
| 6,007,497 A * | 12/1999 | Huitema | 600/567 |
| 6,017,316 A | 1/2000 | Ritchart et al. | |
| 6,019,733 A | 2/2000 | Farascioni | |
| 6,022,324 A * | 2/2000 | Skinner | 600/566 |
| D423,717 S | 4/2000 | Taylor | |
| 6,050,955 A | 4/2000 | Bryan et al. | |
| D426,025 S | 5/2000 | Holmes et al. | |
| 6,077,230 A * | 6/2000 | Gregoire et al. | 600/566 |
| 6,080,113 A | 6/2000 | Heneveld et al. | |
| 6,085,749 A | 7/2000 | Wardle et al. | |
| 6,086,544 A * | 7/2000 | Hibner et al. | 600/568 |
| 6,096,042 A * | 8/2000 | Herbert | 606/80 |
| 6,106,484 A * | 8/2000 | Terwilliger | 600/568 |
| 6,109,446 A | 8/2000 | Foote | |
| 6,120,462 A * | 9/2000 | Hibner et al. | 600/566 |
| 6,120,463 A | 9/2000 | Bauer | |
| 6,123,299 A | 9/2000 | Zach, Sr. | |
| 6,142,955 A | 11/2000 | Farascioni et al. | |
| 6,162,187 A * | 12/2000 | Buzzard et al. | 600/573 |
| 6,193,414 B1 | 2/2001 | Balzano | |
| 6,193,673 B1 * | 2/2001 | Viola et al. | 600/568 |
| 6,273,862 B1 * | 8/2001 | Privitera et al. | 600/568 |
| 6,293,957 B1 | 9/2001 | Peters et al. | |
| 6,346,107 B1 | 2/2002 | Cucin | |
| 6,402,701 B1 * | 6/2002 | Kaplan et al. | 600/567 |
| 6,416,484 B1 * | 7/2002 | Miller et al. | 600/564 |
| 6,428,487 B1 * | 8/2002 | Burdorff et al. | 600/568 |
| 6,461,350 B1 | 10/2002 | Underwood et al. | |
| 6,468,225 B1 * | 10/2002 | Lundgren | 600/562 |
| 6,468,227 B2 | 10/2002 | Zimmon | |
| 6,485,436 B1 * | 11/2002 | Truckai et al. | 600/564 |
| 6,626,850 B1 * | 9/2003 | Chau et al. | 600/567 |
| 6,632,182 B1 * | 10/2003 | Treat | 600/564 |
| 6,752,768 B2 * | 6/2004 | Burdorff et al. | 600/568 |
| 7,226,424 B2 | 6/2007 | Ritchart et al. | |
| 2001/0014785 A1 | 8/2001 | Sussman et al. | |
| 2002/0082519 A1 * | 6/2002 | Miller et al. | 600/566 |

OTHER PUBLICATIONS

Steven K. Wagner, "Imagin News," Breast ultrasound spurs biopsy technology race, (Mar. 6, 1996).

Publication in Design News entitled "Probe reduces breast biopsy trauma" by Joseph Ogando dated Aug. 7, 2000.

International Search Report No. PCT/US01/51235 dated Dec. 10, 2002.

* cited by examiner

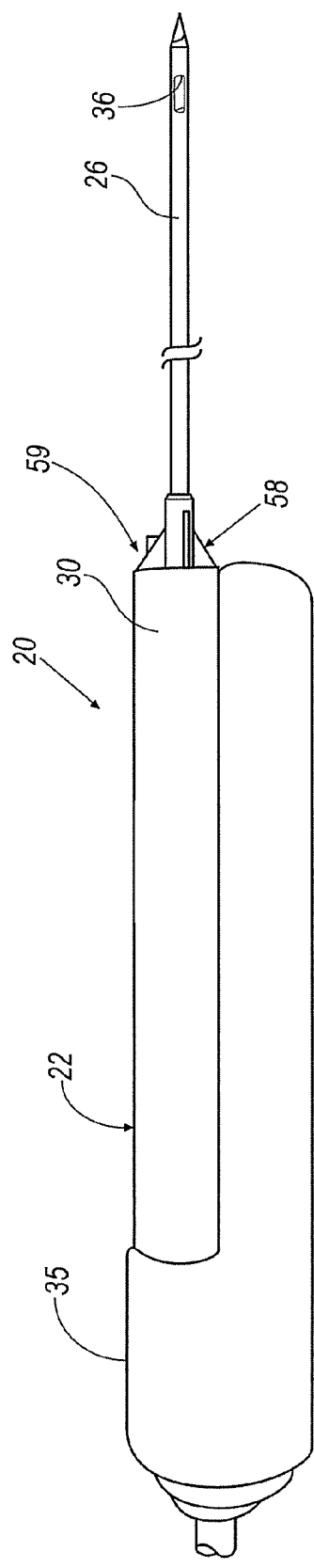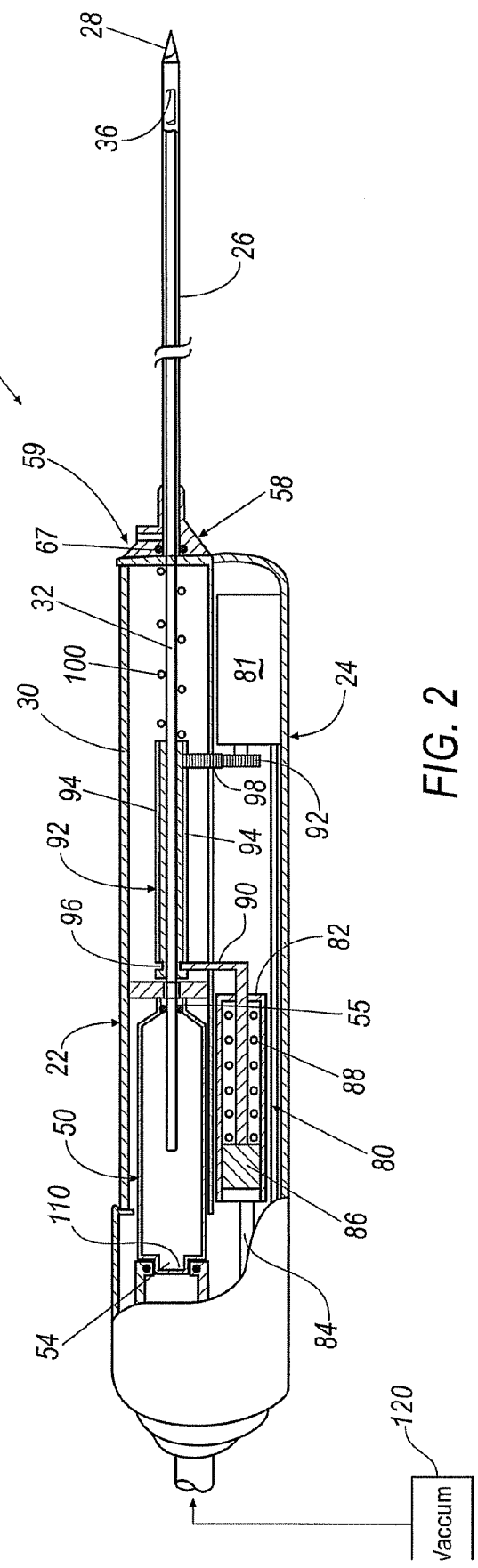

BIOPSY APPARATUS

RELATED APPLICATIONS

This application claims the benefit of U.S. Provisional Patent Application No. 60/490,916 filed Jul. 29, 2003. This application is also a continuation-in-part of U.S. patent application Ser. No. 10/848,278, filed on May 18, 2004, which is a divisional of U.S. patent application Ser. No. 09/707,022, filed on Nov. 6, 2000, now U.S. Pat. No. 6,758,824.

BACKGROUND OF THE INVENTION

1. Field of the Invention

The present invention relates generally to biopsy instruments and methods for taking a biopsy. More particularly, this invention relates to a biopsy apparatus having reusable components for removing several tissue samples using a single insertion.

2. Description of the Related Art

In the diagnosis and treatment of breast cancer, it is often necessary to remove multiple tissue samples from a suspicious mass. Prior to removal, the suspicious mass it generally evaluated by taking a biopsy to determine if the mass is malignant or benign. Early diagnosis of breast cancer, for example, as well as other forms of cancer, can prevent the spread of the disease to other parts of the body.

An exemplary handheld biopsy apparatus is disclosed in U.S. Pat. Nos. 6,758,824 and 6,638,235, the disclosures of which are incorporated by reference, in their entirety. The exemplary biopsy apparatus is a minimally invasive biopsy instrument. Unlike previous biopsy apparatus devices, the exemplary biopsy apparatus is a lightweight, pneumatically controlled disposable hand-piece having a non-clogging and non-occluding cutting blade design. The hand-piece and cutting blade are compatible with multiple visualization techniques, including without limitation, Magnetic Resonance Imaging (currently the only non-invasive visualization modality capable of defining the margins of a suspicious mass or tumor). This MRI compatibility is generally due to the fact that the entire biopsy apparatus is made out of components that do not interfere with operation of the MRI device or are otherwise incompatible with the MRI environment. A unique tissue collection system is used to aid in capture, location, identification and staging of the biopsy sample, and retains histological and pathological viability of the removed tissue without exposing the medical staff to the patient's body fluids. The exemplary biopsy apparatus is fully automated, preserves surgical accuracy and affords a surgeon greater surgical flexibility.

Although the exemplary biopsy apparatus disclosed in pending U.S. patent applications, Ser. Nos. 09/707,022 and 09/864,031, represents a significant advancement in the field of medical biopsy, the entire biopsy apparatus must be disposed of after the medical procedure, even if a portion of the biopsy apparatus is not exposed to bio-hazardous materials. Because there is an economic disincentive to dispose of potentially reusable components, a need exists for an improved biopsy apparatus that incorporates the advancements of the exemplary biopsy apparatus described above into a partially reusable design.

SUMMARY OF THE INVENTION

The present invention is directed to a biopsy apparatus that has a disposable cutting element. The cutting element includes an outer cannula defining an outer lumen, a tissue-receiving opening that is positioned proximate to a distal end of the outer cannula that communicates with the outer lumen, and an inner cannula slidably disposed within the outer lumen and defining an inner lumen from an open distal end to an open proximal end opposite the distal end. The inner cannula also includes a cutting edge at the open distal end operable to sever the tissue projecting through the tissue-receiving opening.

In accordance with one aspect of the invention, the biopsy apparatus includes a reusable handpiece. The disposable cutting element is releasably connected to the reusable handpiece. In accordance with another aspect of the invention, the reusable handpiece further includes a first MRI compatiable device that is detachably connected to the inner cannula to rotate the inner cannula within the outer cannula. The reusable handpiece also includes a second MRI compatible device that is detachably coupled to the inner cannula to translate the inner cannula within the outer cannula while the inner cannula rotates.

BRIEF DESCRIPTION OF THE DRAWINGS

Embodiments of the invention will now be described, by way of example, with reference to the accompanying drawings, wherein:

FIG. 1 is a side view of a biopsy apparatus according to an embodiment of the present invention.

FIG. 2 is a simplified cross-sectional illustration of the biopsy apparatus of FIG. 1.

DETAILED DESCRIPTION

Figure 4:
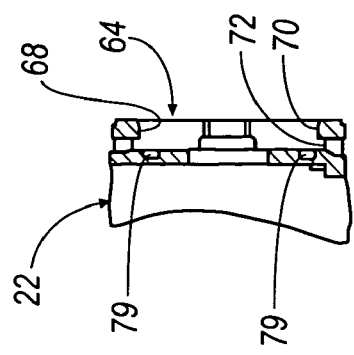
FIG. 4 is a side cross-sectional view of an end of a disposable housing of the present invention.
Figure 7:
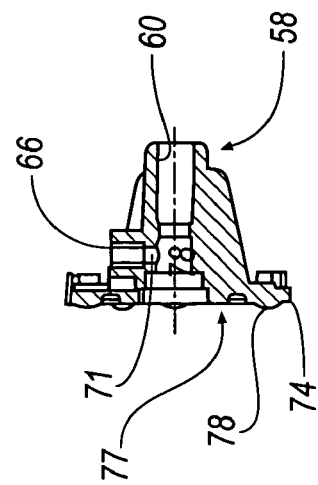
FIG. 7 is a cross-sectional view of the hub of FIG. 5.

Referring now to the drawings, the preferred illustrative embodiments of the present invention are shown in detail. Although the drawings represent some preferred embodiments of the present invention, the drawings are not necessarily to scale and certain features may be exaggerated to better illustrate and explain the present invention. Further, the embodiments set forth herein are not intended to be exhaustive or otherwise limit or restrict the invention to the precise forms and configurations shown in the drawings and disclosed in the following detailed description.

The present invention concerns an apparatus for excising one or more tissue samples during a biopsy procedure, such as a biopsy of a human breast. A biopsy apparatus 20 in accordance with an embodiment of the present invention is shown in FIGS. 1 and 2. Apparatus 20 includes a disposable cutting element or cartridge 22 removably mounted to a reusable handpiece 24. Cutting element 22 and the overall biopsy apparatus 20 are configured for ease of use in the surgical environment. In the illustrated embodiment, biopsy apparatus 20 is configured as a hand-held device. However, the same inventive principles may be employed in a tissue biopsy apparatus that is used stereotactically, wherein the apparatus is mounted in a support fixture that is used to position cutting element 22 relative to the tissue to be sampled.

Cutting element 22 is configured as a "tube-within-a-tube" cutting device. More specifically, cutting element 22 includes an outer cannula 26 terminating in a tip 28. In one particular configuration, tip 28 is a trocar tip that can be used to penetrate a patient's skin. Alternatively, tip 28 can simply operate as a closure for an open end of outer cannula 26. In this instance, a separate introducer would be required.

Figure 3:
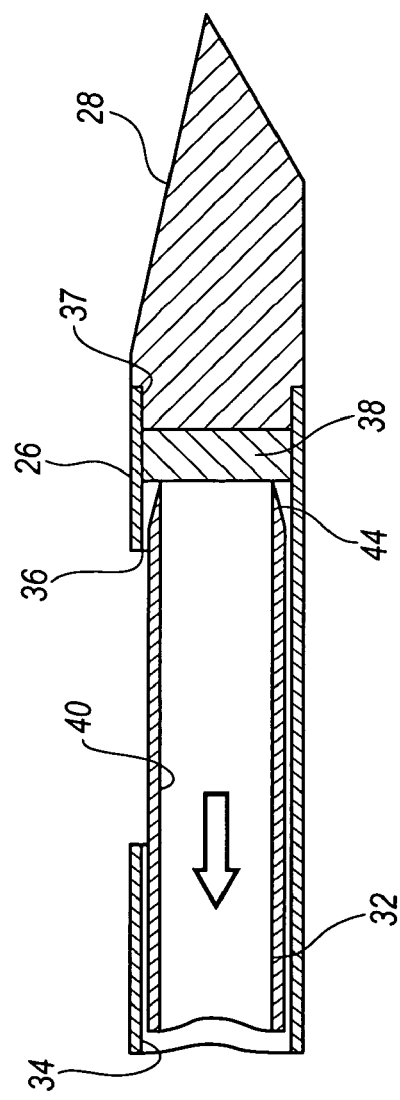
FIG. 3 is an enlarged side cross-sectional view of an operating end of the biopsy apparatus depicted in FIGS. 1 and 2.
Figure 6:
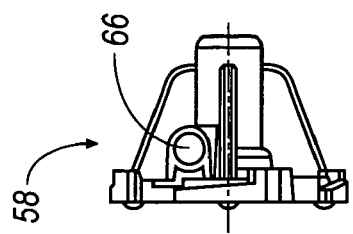
FIG. 6 is a side elevation view of the hub of FIG. 5.
Figure 5:
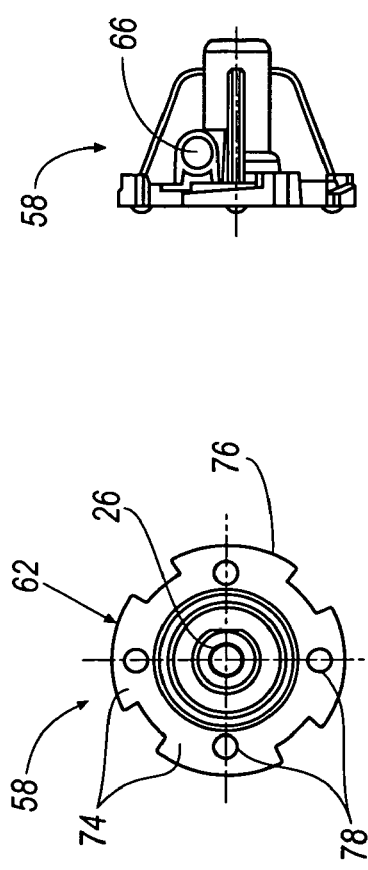
FIG. 5 is an end elevation view of a hub according to an embodiment of the invention.

Cutting element 22 further includes a disposable housing 30 and an inner cannula 32 that fits concentrically within an outer lumen 34 of outer cannula 26 (see FIG. 3). Depending on the manner in which cutting element 22 is affixed to handpiece 24, cutting element 22 may be detached by sliding housing 30 off of an end 35 of handpiece 24. Alternatively, ergonomic attachment 32 may be removed by applying a pivoting force up and away from handpiece 24, thus providing a "snap off" detachment. Either or both of housing 30 and handpiece 24 may include, for example, grooves, ridges, bumps, dimples and other suitable features that provide a detent or other engagement feature that secures one component to the other. However, other approaches for removably securing cutting element 22 to handpiece 24, such as screw-type fasteners, for example, are also within the scope of present invention.

Referring to FIG. 3, outer cannula 26 defines a tissue-receiving opening 36 that communicates with outer lumen 34. A pair of opposite longitudinal edges define the tissue receiving opening 36. The length of tissue receiving opening 36 generally determines the length of the biopsy sample extracted from the patient. Outer cannula 26 is open at its distal end 37 with trocar tip 28 engaged therein. Outer cannula 26 may also include a cutting board 38 that is at least snugly disposed within outer lumen 26 at the distal end of outer cannula 26.

Inner cannula 32 is at least partially supported by housing 30 or a component within housing 30 for sliding and rotational movement therein. In one embodiment, inner cannula 32 defines an inner lumen 40 that is hollow along its entire length to provide for aspiration of the biopsy sample. Inner cannula 32 terminates in a cutting edge 42. In one embodiment, cutting edge 42 is formed by an inwardly beveled surface 44 to provide a razor-sharp edge. The inwardly beveled surface 44 reduces the risk of catching edge 42 on the tissue-receiving opening 36 of outer cannula 26. Additionally, the beveled surface 44 helps avoid pinching the biopsy material between the inner and outer cannulae 32, 26 during a cutting stroke.

The configuration of inner cannula 32 and outer cannula 26 is not limited to that shown in the drawings. Alternatively, inner and outer cannulae 32, 26 may include other features that facilitate repeatable and precise withdrawal of a tissue sample from a patient. For example, a number of teeth can be formed at each longitudinal edge of tissue receiving opening 36. In another example, a stiffening element can be incorporated into outer cannula 26 opposite the tissue receiving opening to add bending stiffness and maintain the longitudinal integrity of outer cannula 26. In still another example, a dimple may be incorporated into outer cannula 26 to prevent cutting edge 42 of inner cannula 32 from catching on outer cannula 26 as it traverses tissue-receiving opening 36. The above-described alternative configurations of inner and outer cannulae 32, 26 are disclosed in detail in U.S. Pat. Nos. 6,758,824 and 6,638,235.

Both inner and outer cannulae 32, 26 may be formed of a surgical grade metal, such as stainless steel. However, when magnetic resonance imaging (MRI) compatibility is required, the cannulae can be formed of inconel, titanium and other materials with similar magnetic characteristics.

Cutting board 38 is formed of a material having properties that reduce the friction between cutting edge 42 of inner cannula 32 and cutting board 38. The cutting edge 42 necessarily bears against the cutting board 38 when inner cannula 32 is at the end of its stroke while severing tissue that has prolapsed into outer cannula 26. Since inner cannula 32 is also rotating, cutting edge 42 necessarily bears directly against cutting board 38, particularly after the tissue sample has been cleanly severed. In one embodiment, cutting board 38 is formed of a material that is physically softer than the material of cutting edge 42. However, cutting board 38 cannot be so soft that the cutting edge 42 forms a pronounced circular groove in the cutting board, which significantly reduces the cutting efficiency of inner cannula 32. For example, cutting board may be formed of a plastic material, such as polycarbonate, ABS and the like.

Since the inner cannula 32 provides an avenue for aspiration of a biopsy sample, the invention further contemplates a collection trap 50 that is removably secured to cutting element 22. In one particular configuration, collection trap 50 includes a filter 110 that permits fluid to pass while retaining the severed tissue within the trap and a pilot port 54 that is connected by appropriate tubing to a control system, as will be described in more detail herein. The control system provides a vacuum or aspiration pressure through pilot port 54 and the collection trap 50. The vacuum source 120 draws a tissue sample excised at the working end of cutting element 22, and accompanying fluids, all the way through inner cannula 32 until it is deposited in collection trap 50. An annular sealing element 55, such as an o-ring, may be disposed between collection trap 50 and inner cannula 32 to inhibit fluid leakage.

Referring to FIGS. 4-7, outer cannula 26 is supported by a hub 58 mounted to the distal end 59 of disposable housing 30. In one embodiment, hub 58 is configured to introduce fluids into outer lumen 34. In one configuration, hub 58 includes an engagement bore 60 within which outer cannula 26 is engaged. Hub 58 also defines a flange 62 configured for mating with a fitting 64 at distal end 59 of disposable housing 30 and an irrigation fitting 66 having an irrigation lumen 71 that communicates with engagement bore 60. An annular sealing member 67 (see FIG. 2) seals against inner cannula 32 to inhibit fluids from leaking into housing 30.

Hub 58 may also be configured to be removably attached to housing 30. In the illustrated embodiment, fitting 64 includes a circumferential recess 68 and a number of spaced flanges 70. In one configuration, four of such flanges are spaced at 90° intervals. Recess 68 defines an enlarged gap 72 between one pair of flanges. Hub 58 also includes a number of wings 74 corresponding in number to flanges 70. Each wing 74 is configured to fit into the recess 68 between the flanges. One of the wings includes an enlargement 76 that prevents the hub from being improperly oriented, or more specifically, ensures a pre-determined orientation of the tissue receiving opening of outer cannula 26. The ability to disconnect hub 58 and outer cannula 26 from housing 30 allows a surgeon to create a pathway to the biopsy site through outer cannula 26. This pathway can be used to place various devices at the biopsy site, including without limitation, a site marker.

The bottom surface 77 of hub 58 also includes a number of protuberances 78. Each of the protuberances is sized to fit within a retention dimple 79 of fitting 64. Thus, when hub 58 is pushed into recess 68 and rotated, each of the protuberances 78 engages within a corresponding dimple 79 to hold hub 58 in place.

In one particular embodiment, biopsy apparatus 20 includes a secondary lumen that engages hub 58. Ultimately, the irrigation lumen is in fluid communication with the outer lumen 34 of outer cannula 26. The secondary lumen can be used to supply a quantity of irrigation fluid or a measured quantity of air to the biopsy site via outer cannula 26. Hub 58 thus provides a mechanism for introducing specific fluids to the biopsy site. In certain procedures, it may be necessary to introduce additional anesthetic to the sampling site, which can be readily accommodated by the irrigation fitting.

As noted above, the present invention contemplates an inner cannula 32 that performs its cutting operation by both rotary and reciprocating motion. Thus, reusable handpiece 24 includes a reciprocating device 80 to translate inner cannula 32 within outer cannula 26, and a rotary motor 81 to drive rotation of inner cannula 32. In one embodiment, device 80 and motor 81 are hydraulically powered, such as pneumatically. This feature allows device 80 and motor 81 to be formed of MRI compatible materials, such as plastic. In fact, in accordance with one aspect of the invention, every component of biopsy apparatus 20 can be made of non-metallic or MRI compatible materials so that biopsy apparatus 20 is eminently compatible with various surgical imaging systems, including without limitation, MRI, ultrasound and X-ray. The compatibility of biopsy apparatus 20 with MRI is desirable because MRI is currently the only non-invasive visualization modality capable of defining the margins of a tumor. Additionally, the elimination of relatively heavy materials reduces the overall weight of the handpiece, making the apparatus 20 easier to manipulate by a surgeon.

In one particular embodiment, reciprocating device 80 includes a pneumatic cylinder 82 having a pilot port 84 that connects cylinder 82 to a control system through appropriate tubing. A piston 86 is disposed within cylinder 82 for reciprocating movement in response to hydraulic fluid pressure provided at pilot port 84. A resilient biasing member 88, such as a compression spring, is received within cylinder 82 and provides a biasing force against piston 86. Alternatively, cylinder 82 may include two pilot ports on opposite sides of piston 86, in lieu of resilient biasing member 88, to provide fluid power to move piston 86 in each direction.

A push rod 90 is engaged on one end with piston 86 and on the other end with a drive gear 92 secured to inner cannula 32. In a particular configuration, drive gear 92 is generally cylindrical in shape having a plurality of longitudinally extending gear teeth 94 and an annular recess 96. The end of push rod 90 engaging drive gear 92 is forked, which allows it to be received in annular recess 96. Gear teeth 94 are meshed with an idler gear 98 disposed between motor 81 and drive gear 92. Alternatively, drive gear 92 may be directly driven by motor 81 without the use of an idler gear.

Reciprocating movement of inner cannula 32 is therefore effectuated by movement of piston 86 within cylinder 82. Additionally, rotation of inner cannula 32 is effectuated by operation of motor 81 and the corresponding rotation of idler gear 98 meshing with drive gear 92. As drive gear 92 and inner cannula 32 reciprocate within cutting element 22, idler gear 98 remains meshed with elongated gear teeth 94, allowing drive gear 92 and inner cannula 32 to rotate as they translate.

As will be appreciated, drive gear 92 is easily connected to push rod 90 and idler gear 98 as cutting element 22 is attached to reusable handpiece 24. Optionally, a resiliently compressible member 100, such as a compression spring, may be positioned between drive gear 92 and housing 30 over inner cannula 32 to facilitate proper alignment of drive gear 92 with push rod 90.

As noted above, the illustrated embodiment of apparatus 20 relies on fluid power to drive the cutting action of inner cannula 32. However, in an alternate embodiment of the invention, rotary motor 81 may comprise an electric motor, rather than a fluid power operated motor. In another alternate embodiment, reciprocating device 80 may comprise a rotary motor drivingly connected to inner cannula 32 via a drive mechanism, such as a rack and pinion arrangement. In either case, use of an electric motor is not necessarily an option when biopsy apparatus 20 is to be use in an MRI-type environment.

While biopsy apparatus 20 can be operated to remove a single tissue sample, the features of the present invention allow the complete removal of a tissue mass through successive cutting and aspiration. In one typical procedure, a portion of cutting element 22 is positioned directly adjacent a tissue mass using an imaging system, such as MRI. Biopsy apparatus 20 is then operated to successively remove pieces of the mass while the excised tissue is continuously drawn into the cutting element 22 by the aspiration pressure or vacuum drawn through inner cannula 32. Successive reciprocation of inner cannula 32 removes large pieces of the mass until it is completely removed.

To facilitate this continuous cutting feature, a control system is provided in communication with handpiece 24. An exemplary control system for use with biopsy apparatus 20 is disclosed in U.S. Pat. Nos. 6,758,824 and 6,638,235, although the control system used for controlling biopsy apparatus 20 is not necessarily limited thereto. The control system controls operation of reciprocating device 80 and the rotary motor 81 to drive movement of inner cannula 32. In a method of operating apparatus 20, control system provides a complete system for continuously reciprocating inner cannula 32. In addition, the control system provides continuous pressure to both rotary motor 81 and the aspiration line under the physician's direction. Regarding the reciprocating device 80, control system provides at least two control functions: (i) the ability to selectively activate reciprocating device 80; and (ii) the ability to control the fluid flow rate to piston 86.

Use of a fluid controlled inner cutting cannula 32 provides significant advantages over prior tissue cutting devices. The use of hydraulics eliminates the need for electrical components, which means that electrical insulation is unnecessary to protect the patient and that the device is compatible with MRI. Additionally, the fluid controlled reciprocation of the inner cannula 32 provides a cleaner and better-controlled cut of the biopsy tissue. Since the pressure in cylinder 80 increases as piston 86 advances, the piston advances at a controlled rate against spring 88. This allows inner cannula 32 to advance through the biopsy tissue at a rate determined by the tissue itself. In other words, when cutting edge 42 encounters harder tissue during a cutting stroke, the rate of advancement of piston 86 and inner cannula 32 decreases proportionately. This feature allows cutting edge 42 to slice cleanly through the tissue without the risk of simply pushing the tissue. The rotation of the cutting edge 42 can facilitate this slicing action. When inner cannula 32 encounters less dense tissue, the constant pressure behind piston 86 allows the cutting edge to advance more quickly through the tissue.

It will also be appreciated that biopsy apparatus 20 of the present invention provides a complete "closed" tissue excision and recovery system. Unlike some prior art biopsy apparatuss, cutting element 22 is fluid tight so that no bodily fluids can escape. Biopsy procedures with prior art devices involve significant blood splatter due to the "open" nature in which the tissue samples are extracted and recovered. This is particularly important where a portion of the biopsy apparatus is reusable, as in the present invention, and there is zero tolerance for bodily fluids coming in contact with the reusable portion of the apparatus. With the present invention, the biopsy apparatus 20 provides a closed path from the tissue receiving opening to the collection trap 50 in a disposable package, while still maintaining the highly efficient reciprocating and rotating cutting operation. Moreover, the handpiece portion of biopsy apparatus 20 is reusable as only cutting element 22 is disposed of after the biopsy procedure.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A biopsy apparatus, comprising:
   a disposable cutting element and a reusable handpiece;
   wherein the disposable cutting element includes an outer cannula defining an outer lumen, a tissue-receiving opening proximate a distal end of the outer cannula communicating with the outer lumen, and an inner cannula slidably disposed within the outer lumen and defining an inner lumen from an open distal end to an open proximal end opposite the distal end, wherein the inner cannula includes a cutting edge at the open distal end operable to sever tissue projecting through the tissue-receiving opening, and a tissue aspiration path in the inner lumen from the open distal end of the inner cannula to the open proximal end of the inner cannula; and
   wherein the reusable handpiece includes a first MRI compatible device detachably coupled to said inner cannula to rotate the inner cannula within the outer cannula, and a second MRI compatible device detachably coupled to the inner cannula to translate the inner cannula within the outer cannula while the inner cannula rotates, wherein the second MRI compatible device includes a hydraulic cylinder and a piston slidably disposed within said cylinder.

2. The biopsy apparatus of claim 1, further including a return spring disposed within the cylinder and biased against the piston to move the piston, and the inner cannula in a predetermined direction away from the distal end of the outer cannula.

3. The biopsy apparatus of claim 1, further comprising a vacuum source in fluid communication with the open proximal end of the inner cannula such that when the vacuum source is activated, severed tissues samples are aspirated through the open proximal end of the inner cannula.

4. The biopsy apparatus of claim 3, further including a tissue collection chamber removably mounted to the handpiece and interposed between the vacuum source and an end of the inner cannula to receive severed tissue drawn into the chamber by the vacuum.

5. The biopsy apparatus of claim 4, wherein the tissue collection chamber includes a filter that permits fluid to pass while retaining the severed tissue within the chamber.

6. The biopsy apparatus of claim 1, wherein the disposable cutting element snaps into the reusable handpiece.

7. The biopsy apparatus of claim 1, wherein the cutting element is slidingly engaged with the reusable handpiece.

8. The biopsy apparatus of claim 1, wherein the inner and outer cannulae are constructed of inconel or titanium.

9. The biopsy apparatus of claim 1, wherein the cutting edge of the cutting element is an inwardly beveled surface.

10. The biopsy apparatus of claim 1 further including a trocar tip.

11. The biopsy apparatus of claim 10, wherein the trocar tip has an engagement hub configured to fit tightly within the distal end of the outer cannula.

12. The biopsy apparatus of claim 11, wherein the hub includes an irrigation fitting having an irrigation lumen.

13. The biopsy apparatus of claim 1, further including a cutting board disposed at the distal end of the outer cannula.

14. The biopsy apparatus of claim 13, wherein the cutting board is affixed to an engagement hub that is affixed to a trocar tip.

15. The biopsy apparatus of claim 1, further comprising a drive gear disposed about a portion of the length of the inner cannula and having a plurality of longitudinally extending gear teeth.

16. The biopsy apparatus of claim 15, wherein the first MRI compatible device comprises an actuating gear detachably engaged to the drive gear such that when the actuating gear engages the drive gear and rotates, the drive gear rotates, thereby causing the inner cannula to rotate within the outer cannula.

17. The biopsy apparatus of claim 15, wherein the second MRI compatible device comprises a piston and a push rod, wherein the push rod has a first end engaged to the piston and a second end detachably engaged to the drive gear.

18. The biopsy apparatus of claim 17, wherein the drive gear comprises an annular recess and the second end of the push rod detachably engages the annular recess.

19. The biopsy apparatus of claim 1, further comprising a drive gear having first and second ends and a plurality of longitudinal teeth disposed about a portion of the length of the inner cannula, wherein the first MRI compatible device is a hydraulic rotary motor that is detachably coupled to the drive gear and the second MRI compatible device is a hydraulic reciprocating motor that is detachably coupled to the drive gear adjacent the first end of the drive gear, and the hydraulic reciprocating motor comprises a hydraulic cylinder and a piston slidably disposed within the cylinder such that translation of the piston within the hydraulic cylinder causes the inner cannula to translate within the outer cannula as the inner cannula rotates.

20. A biopsy apparatus, comprising:
    a disposable cutting element detachably connected to a reusable handpiece;
    wherein the disposable cutting element includes an outer cannula defining an outer lumen, a tissue-receiving opening proximate a distal end of the outer cannula communicating with the outer lumen, an inner cannula slidably disposed within the outer lumen and defining an inner lumen from an open distal end to an open proximal end opposite the distal end, and a drive gear disposed about a portion of a length of the inner cannula and having a plurality of longitudinally extending teeth, wherein the inner cannula includes a cutting edge at the open distal end operable to sever tissue projecting through the tissue-receiving opening, and a tissue aspiration path in the inner lumen that passes through the drive gear; and
    wherein the reusable handpiece includes a hydraulic rotary motor detachably coupled to said inner cannula by said drive gear to rotate the inner cannula within the outer cannula, and a hydraulic reciprocating motor detachably coupled to the inner cannula to translate the inner cannula within the outer cannula while the inner cannula rotates.

21. The biopsy apparatus of claim 20, wherein the disposable cutting element snaps into the reusable handpiece.

22. The biopsy apparatus of claim 20, wherein the cutting element is slidingly engaged with the reusable handpiece.

23. The biopsy apparatus of claim 20, wherein the inner and outer cannulae are constructed of inconel or titanium.

24. The biopsy apparatus of claim 20, wherein the hydraulic rotary motor and the hydraulic reciprocating motor are constructed of a material that is compatible with MRI.

25. The biopsy apparatus of claim 20 further including a vacuum source fluidly connected to the inner cannula for generating a vacuum in the lumen of the inner cannula to draw severed tissue through the open distal end of the inner cannula and the open proximal end of the inner cannula, and a tissue collection chamber positioned between the vacuum source and an end of the inner cannula to receive severed tissue drawn into the chamber by the vacuum.

26. A biopsy apparatus, comprising:
a disposable cutting element and a reusable handpiece;
wherein the disposable cutting element includes an outer cannula defining an outer lumen, a tissue-receiving opening proximate a distal end of the outer cannula communicating with the outer lumen, and an inner cannula slidably disposed within the outer lumen and defining an inner lumen from an open distal end of the inner cannula to an open proximal end of the inner cannula opposite the distal end of the inner cannula, the inner cannula includes a cutting edge at the open distal end that is operable to sever tissue projecting through the tissue-receiving opening, the disposable cutting element further includes a drive gear having first and second ends and a plurality of longitudinal teeth disposed about a portion of a length of the inner cannula, a tissue aspiration path in the inner lumen from the open distal end of the inner cannula to the open proximal end of the inner cannula, and a tissue collection chamber with a filter, such that the open proximal end of the inner cannula is disposed in the tissue collection chamber;
wherein the reusable handpiece includes an MRI compatible hydraulic rotary motor detachably coupled to the drive gear to rotate the inner cannula within the outer cannula, and an MRI compatible hydraulic reciprocating motor, and the hydraulic reciprocating motor comprises a hydraulic cylinder, a piston slidably disposed in the hydraulic cylinder, and a push rod having a first end connected to the piston and a second end detachably coupled to the drive gear adjacent the first end of the drive gear to translate the inner cannula within the outer cannula while the inner cannula rotates.

* * * * *

UNITED STATES PATENT AND TRADEMARK OFFICE
CERTIFICATE OF CORRECTION

PATENT NO.        : 7,458,940 B2                                                        Page 1 of 1
APPLICATION NO. : 10/903305
DATED             : December 2, 2008
INVENTOR(S)       : Michael E. Miller It is certified that error appears in the above-identified patent and that said Letters Patent is hereby corrected as shown below:

In Claim 9, line 4, please change [[cuffing]] to cutting.

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,458,940 B2                                    Page 1 of 1
APPLICATION NO.  : 10/903305
DATED            : December 2, 2008
INVENTOR(S)      : Michael E. Miller It is certified that error appears in the above-identified patent and that said Letters Patent is hereby corrected as shown below:

Column 8, In Claim 9, line 4, please change [[cuffing]] to cutting.

This certificate supersedes the Certificate of Correction issued February 10, 2009.

Signed and Sealed this

Tenth Day of March, 2009

JOHN DOLL
*Acting Director of the United States Patent and Trademark Office*